United States Patent [19]

Ragsdale et al.

[11] Patent Number: 5,607,395
[45] Date of Patent: Mar. 4, 1997

[54] DEVICE FOR REMOTE INJECTION OF ANIMALS

[76] Inventors: Ronald Ragsdale, HC 86 P.O. Box 31, Elm Springs, S. Dak. 57736; Daniel Gerbec, 7395 Pinon Jay Cir., Rapid City, S. Dak. 57702

[21] Appl. No.: 382,646

[22] Filed: Feb. 2, 1995

[51] Int. Cl.⁶ .................................................. A61M 5/20
[52] U.S. Cl. ........................... 604/130; 604/135; 40/300
[58] Field of Search .......................... 40/300, 301, 302; 119/858, 860, 906; 604/135, 130, 134

[56]  References Cited

U.S. PATENT DOCUMENTS

| | | | |
|---|---|---|---|
| 2,854,925 | 10/1958 | Crockford | 273/418 |
| 3,042,406 | 7/1962 | Gregory | 273/106.5 |
| 3,982,536 | 9/1976 | Krogseng | 128/260 |
| 4,106,770 | 8/1978 | Gray | 273/106.5 |
| 4,121,586 | 10/1978 | Lawrence | 128/215 |
| 4,182,327 | 1/1980 | Haley | 128/215 |
| 4,312,347 | 1/1982 | Magoon | 128/260 |
| 4,822,340 | 4/1989 | Kamstra | 604/135 |
| 4,863,428 | 9/1989 | Chevalier | 604/130 |
| 5,119,579 | 6/1992 | Hullihen | 43/19 |
| 5,202,533 | 4/1993 | Vandersteen | 102/512 |

OTHER PUBLICATIONS

Various drawings and advertising materials for Cap-Chur remote inoculation syringes of Palmer Chemical and Equipment Company. (Author, title, date, and place of publication unknown.)

Brochure for "StockDoctor" inoculator medicating system for livestock. (Author, title, date, and place of publication unknown.)

*Primary Examiner*—Sam Rimell
*Assistant Examiner*—Jeffrey D. Carlson
*Attorney, Agent, or Firm*—Gene R. Woodle

[57] ABSTRACT

A device for humane injection of fluid into animals from a distance is disclosed. The device comprises a hollow body with a primary chamber suitable for holding the fluid to be injected, a hollow needle at the forward end of the hollow body, a disposable tag attached to the forwardmost surface of the hollow body, and a remote retrieval means. The device may be projected toward the target animal by any of several conventional methods including compressed gas or chemical explosion gun. Upon impact with the target animal a trigger mechanism which comprises a ball and valve seat check valve is tripped allowing a resilient means to force the fluid through the needle and into the animal. The device is held in place during the injection process by an adhesive means on the forwardmost surface of the tag. After injection the device is pulled form the animal using the retrieval means. The tag separates from the device and remains attached to the skin marking the animal.

6 Claims, 3 Drawing Sheets

DEVICE FOR REMOTE INJECTION OF ANIMALS

BACKGROUND

1. Field of Invention

This invention relates to a device for remotely injecting an animal with a liquid.

2. Description of the Related Art

Most large animals both wild and domestic are wary of human contact and are, therefore, difficult to capture when capture is necessary for medical treatment or other purposes. For example, in ranch or feedlot operations cattle often must be injected with a drug or treated for disease or injury. When allowed free range cattle become wary and difficult to catch. Capturing a single animal for injection entails many risks including possible injury to the cow, possible injury to the cowboy, and disruption of the herd which may lead to weight loss or injury to other cattle.

In cases where the intent of capture is injection of a drug or other fluid a method of remote injection is preferable to actual physical capture of the animal. In many instances the animal may be approached to a distance sufficient for remote injection without the disruption and risk of injury caused by physical capture.

Several systems for remote injection of animals have been conceived. Generally such systems involve a missile which may be projected toward the animal from a distance by apparatuses such as crossbows, blowguns, and compressed gas guns. Typically these systems include a barrel with a needle assembly at the forward end. The barrel typically contains a primary chamber at the forward end which holds the fluid to be injected. The primary chamber is typically separated from a secondary chamber at the rearward end of the barrel by a plunger or piston which forms a seal. When the primary chamber is charged or loaded the plunger or piston is pushed rearward and held in place by a trigger mechanism. The secondary chamber ordinarily includes some form of potential energy source such as a compressed spring tending to push the plunger or piston forward. Upon impact of the missile with the target animal the trigger mechanism is tripped allowing the piston or plunger to move forward. The potential energy source in the secondary chamber forces the piston or plunger forward and pushes the fluid through the needle assembly and into the animal.

Several inventions embrace the above describe system to some extent and include a variety of trigger mechanisms and sources of potential energy. Some of the inventions include a method of remote retrieval of the missile and some include a barb on the needle assembly which serves to hold the missile in place during the injection process.

U.S. Pat. No. 3,042,406; Gregory (1962) discloses a missile which generally conforms to the system described above. The trigger mechanism is a spring which holds the plunger in a rearward position when the missile is charged. Potential energy is supplied by elastic bands tending to pull the plunger forward. Upon impact the spring is released which allows the elastic bands to pull the plunger forward. The patent also teaches a compressible collar at the front of the missile. Upon impact the collar compresses and after the injection process is complete the collar regains its uncompressed shape and ejects the needle from the animal.

The patent teaches no method of remote retrieval of the missile and no method of holding the missile in place during the injection process.

U.S. Pat. No. 4,106,770; Gray (1978) discloses a projectile which operates in a manner similar to that described above. The trigger mechanism includes clips or "fingers" which hold the plunger in a rearward position when the projectile is charged and a slideable weight. Potential energy is provided in the form of a spring compressed when the missile is charged. Upon impact the slideable weight moves forward releasing the plunger from the clips and allowing the spring to force the plunger forward.

The patent teaches no method of remote retrieval of the missile and no method of holding the missile in place during the injection process.

U.S. Pat. No. 4,121,586; Lawrence et al. (1978) discloses a dart operating in a manner similar to that described above. The trigger mechanism includes a breakable retaining pin which holds the plunger in a rearward position when the dart is charged. Potential energy is supplied in the form of stretched elastic bands which tend to push the plunger forward. Upon impact the retaining pin breaks allowing the elastic bands to push the plunger forward.

The patent teaches no method of remote retrieval of the missile and no method of holding the missile in place during the injection process.

U.S. Pat. No. 4,182,327; Haley (1980) discloses an apparatus which operates in a manner similar to that described above. The trigger mechanism involves a hollow needle assembly. The rearward end of the needle assembly includes a conical surface which forms a seal with a similar conical surface at the front of the barrel when the needle assembly is in a forward position. Upon impact the needle assembly is forced rearward and held in a rearward position by a clip. With the needle assembly in a rearward position ports in the needle assembly are exposed allowing fluid to flow from the primary chamber through the ports into the needle assembly. Potential energy is supplied in the form of a spring which is compressed when the plunger is pushed rearward.

The patent teaches a barb which serves to hold the apparatus in place in the animal during the injection process and also includes a method of remotely retrieving the apparatus.

U.S. Pat. No. 4,863,428; Chevalier (1989) discloses a dart which operates in a manner similar to that describe above. The trigger mechanism includes a cap which is pushed onto the end of the needle assembly after the dart is charged. The cap prevents fluid from flowing through the needle assembly. Upon impact the needle assembly is pushed through the cap exposing the end of the hollow needle. Potential energy is supplied by a spring in the secondary chamber which is compressed when the dart is charged and the plunger forced rearward.

The patent teaches a barb which serves to hold the apparatus in place in the animal during the injection process, but includes no method of remotely retrieving the apparatus.

U.S. Pat. No. 5,202,533; Vandersteen (1993) discloses an apparatus which operates in a manner similar to that described above. The trigger mechanism involves two O-rings. The first O-ring encircles the perimeter of a release member connected to the plunger by a shaft. A second O-ring is seated inside the perimeter of the barrel. The outside diameter of the first O-ring is greater than the inside diameter of the second. When the plunger is pushed rearward the O-ring on the release member is forced passed the second O-ring, but is held in place and prevented from moving forward by the difference in diameters of the O-rings. Upon impact the O-ring on the release member is pushed passed the second O-ring allowing the plunger to move forward. Potential energy is supplied by a spring in the secondary chamber which is compressed when the apparatus is charged and the plunger is forced rearward.

The patent teaches a remote retrieval method and also includes a ferrule on the needle which acts to hold the apparatus in place during the injection process.

Each of the prior art devices is unsatisfactory for many reasons. Each of the devices includes one or more such unsatisfactory aspects which make them unsatisfactory for field use. Other disadvantages may be apparent to persons reasonably knowledgeable in the art.

Those devices lacking a system for remote retrieval largely defeat the purpose of remote injection. If a target animal is missed or more than one animal is to be injected non-remote retrieval is likely to cause disruption and possibly to cause injury to the device, the animals, or the rancher.

Those devices lacking a barb or ferrule to hold the device in place are likely to be ejected from the animal prior to completion of the injection process.

Those devices having a barb or ferrule to hold the device in place during the injection process are likely to cause skin or tissue damage with concurrent possibilities of infection or disease upon impact or ejection of the device.

The trigger mechanisms of the prior art devices are either complicated and difficult and costly to manufacture or subject to failure on a relatively consistent basis.

The source of potential energy in many of the prior art devices are unnecessarily complicated, must be replaced prior to each injection, or include parts subject to wear and failure.

In may cases loading or charging of prior art devices is unnecessarily complicated and time consuming and often involves at least partial dismantling and reassembly of the device.

SUMMARY OF INVENTION

1. Summary:

The present invention comprises a device for remote injection of liquid into an animal. The device has a hollow body with a forward section and a tail section. The forward section of the body includes a needle assembly having a hollow needle in operative contact with the hollow body.

Within the hollow body there is a slideable piston the front face of which defines a primary chamber suitable for containing the liquid to be injected. The rear face of the piston defines a secondary chamber. Resilient means within the secondary chamber urges the piston toward the primary chamber when the needle enters the animal so as to force the liquid through the needle into the animal.

In the preferred embodiment the device is loaded by pulling back the plunger and drawing fluid through the needle assembly into the primary chamber in much the same manner as with a conventional syringe. A check valve is interposed between the needle assembly and the primary chamber. The check valve comprises an O-ring valve seat in the forward end of the forward section of the hollow body and a ball which fits against the valve seat and prevents the flow of liquid from the primary chamber to the needle assembly when the needle assembly is in the forward or charged position. The ball is held in place against the valve seat by resilient means and by the pressure of the fluid contained within the primary chamber. Upon impact with the target animal the needle assembly is pushed back to a rearward or discharge position. Upon moving rearward the needle assembly pushes the ball rearward away from the valve seat. The needle assembly is locked in discharge position and the hollow needle is then in operational contact with the primary chamber. The unseated ball allows fluid to flow from the primary chamber through the needle assembly into the target animal. Pulling back the plunger to charge the device compresses the resilient means in the secondary chamber.

Another aspect of the invention is a nose cone attached to the front surface of the forward section by a fastening means. The opening of the nose cone faces rearward. There is a hole in the middle of the forwardmost surface of the nose cone. The needle passes through and fits within the hole in the nose cone.

A tag fashioned from a flexible material is connected to the forwardmost surface of the nose cone by a fastening means. The needle passes through a hole in the tag. The forwardmost surface of the tag is coated with adhesive means. Upon impact the adhesive holds the device in place with the needle piercing the animal's skin for the duration of the injection process. The adhesive means is strong relative to the strength of the fastening means connecting the tag to the nose cone. After the injection process is complete the relatively weak fastening means is broken and the device retrieved leaving the tag attached to the animal. The tag remaining on the target animal indicates which animals have been injected and may be color coded to accomplish multiple marking purposes including, but not limited to, the date or type of injection.

The device may be projected toward the target animal by any of several conventional apparatuses including a crossbow, a compressed gas gun, a blowgun, or a long rod. The invention further includes a remote retrieval system consisting of a line connecting the device to the projecting apparatus.

2. Advantages of the Invention:

There are several advantages to the instant invention which will be apparent to a person reasonably knowledgeable in the art. Many, but not all, of those advantages are indicated below.

The invention includes a system for remote injection of animals.

The invention includes a system for retrieval of the remote injection device by remote means in the event that the target animal is missed or more than one animal is to be injected.

The invention includes a ball and valve seat check valve as a part of the trigger mechanism which is very simple, inexpensive and easy to manufacture, reliable, and durable. The check valve operates in a simple and straightforward manner and involves a minimum of complicated or moving parts.

The invention is simple and easy to load or charge. Charging is accomplished quickly with no tools and does not involve disassembly or removal of any parts.

The nose cone is formed in a shape promoting the aerodynamics of the device. The shape of the nose cone further serves to cushion the impact of the device upon contact with the target animal. The shape prevents the needle assembly rearward from the shaft of the needle from piercing the hide of the animal and causing hide and tissue damage. The rearward movement of the nose cone provides some further cushioning of the impact between the target animal and the injection device. The hole in the nose cone provides support to the needle.

The tag accomplishes the object of holding the device in place during the injection process. The tag is disposable, separates from the rest of the device after the injection process is complete, and remains attached to the skin of the animal. After the injection process is complete the tag accomplishes the object of marking which animals have been injected. The tag may also be color coded to indicate data including type or date of injection. Use of the tag to hold the device in place during the injection process eliminates the possibility of damage to the skin or tissue of the animal intrinsic to the use of a barb or ferrule.

BRIEF DESCRIPTION OF THE DRAWINGS

The invention is further described in connection with the accompanying drawings, in which.

DETAILED DESCRIPTION OF THE PREFERRED EMBODIMENT

Figure 1:
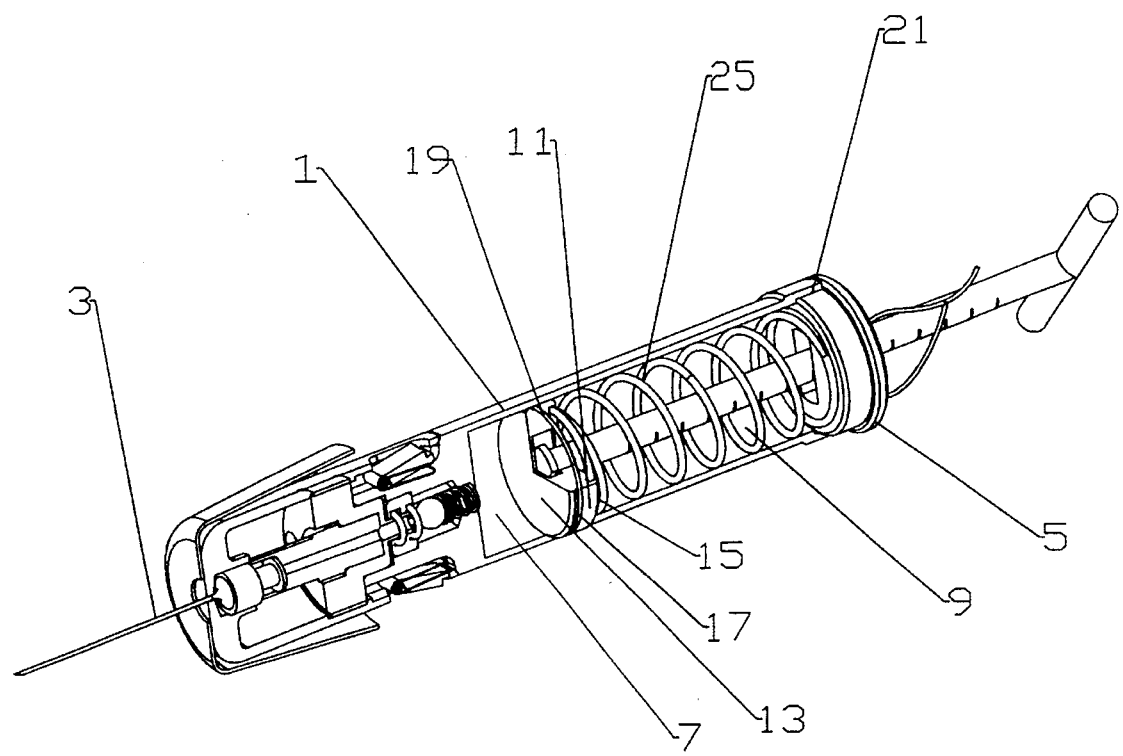
FIG. 1 is a perspective sectional view of the entire invention.

The general layout and configuration of the invention is depicted in FIG. 1. The injection apparatus comprises a cylindrical hollow body I with a hollow needle 3 at the forward end and a tail cover 5 at the rearward end. Inside the hollow body 1 near the forward end is a cylindrical primary chamber 7. Inside the hollow body 1 at the rearward end is a cylindrical secondary chamber 9. The rearward end of the primary chamber 7 is formed by a movable piston 11. A forward face 13 of piston 11 defines the primary chamber 7. A rearward face 15 of piston 11 defines the secondary chamber 9. The piston 11 has a cylindrical outer surface 17 carrying an O-ring 19 to provide a seal. The rear end of the hollow body 1 is internally threaded as indicated at 21. The rear end of the hollow body 1 is closed by the tail cover 5 which is threadably engaged with the end of the hollow body 1 at 21. Inside the secondary chamber 9 is a piston spring 25 which has one end abutting rearward face 15 and a second end abutting the tail cover 5.

Figure 2:
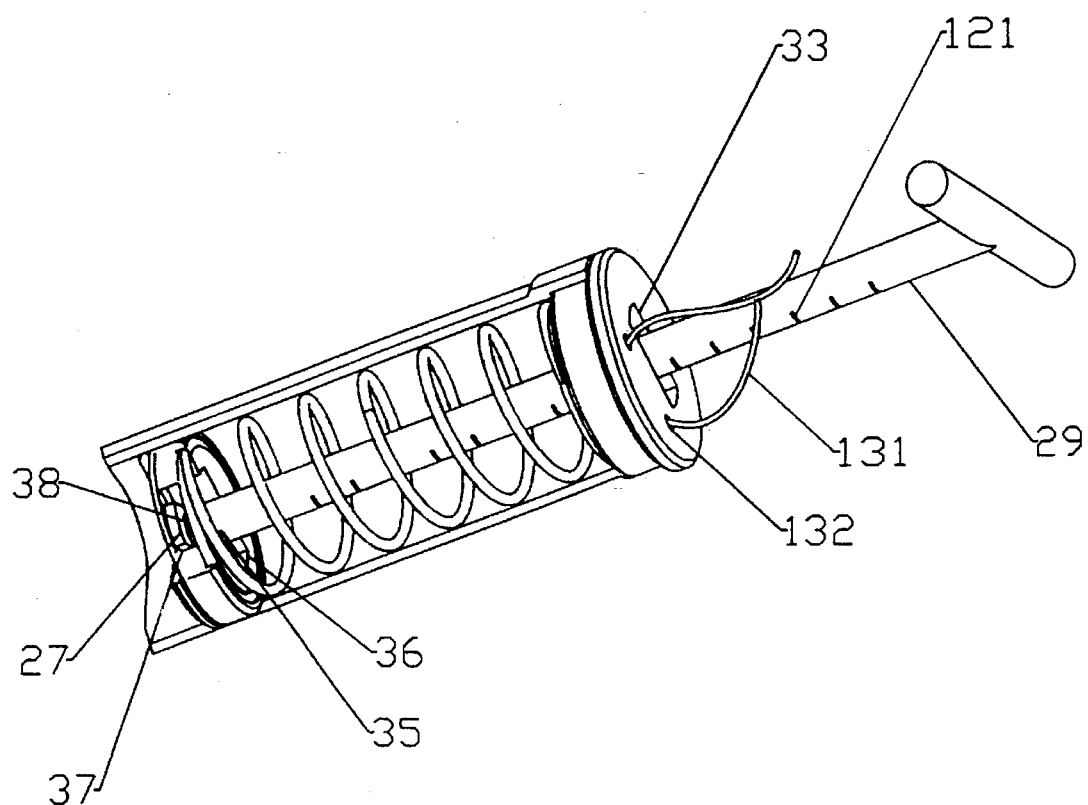
FIG. 2 is an enlarged, rearward, partial, perspective sectional view showing the secondary chamber and enclosed details.

As depicted in FIG. 2 a plurality of prongs 27 at the forward end of a piston rod 29 are insertable through an opening 33 in the tail cover 5. The prongs 27 are further insertable through a piston opening 35 and slots 36 equal in number to the number of prongs 27. The piston rod 29 may be rotated causing the prongs 27 to contact a piston surface 37 inside a piston core 38 and engage the piston rod 29 with the piston 11.

Figure 3:
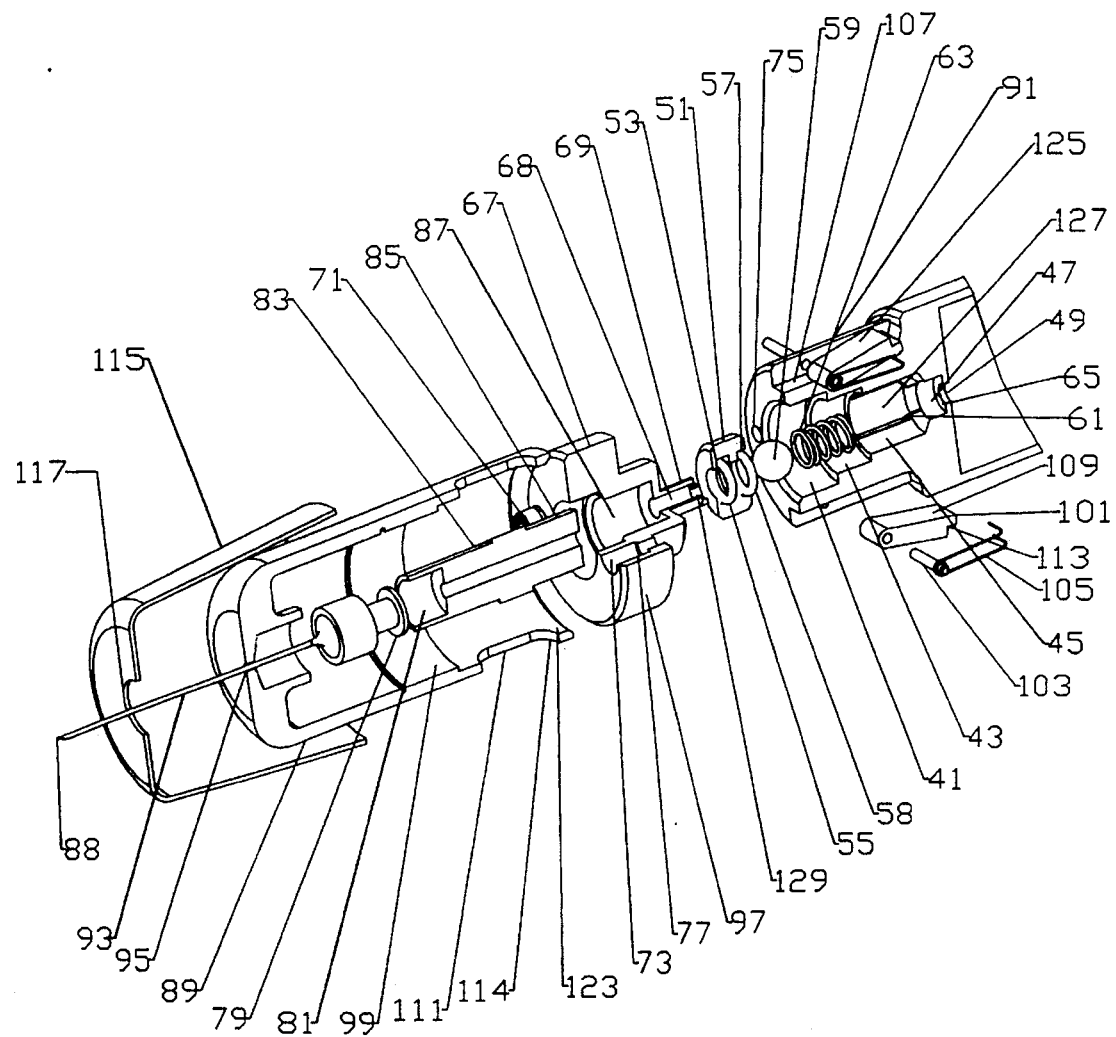
FIG. 3 is an enlarged, exploded, perspective view of the trigger mechanism and the fluid delivery system.

Referring now to FIG. 3 an opening comprising a series of cylindrical apertures of various diameters connects the forwardmost face of the hollow body 1 with the primary chamber 7. The forwardmost of the apertures is indicated at 41, the next forwardmost at 43, the next forwardmost at 45, the next forwardmost at 47, and the most rearward at 49. Aperture 43 is screw threaded. A valve seat 51 is exteriorly screw threaded and screws into aperture 43. An O-ring groove 53 inside valve seat 51 carries an O-ring 55 providing a seal. Another O-ring groove 57 at the rearward end of the valve seat 51 carries an O-ring 58 providing a seal. Inside aperture 47 is a ball 59. The ball 59 is moveable from a forward position against O-ring 58 to a rearward position against a shoulder 61 inside aperture 47. A ball spring 63 abuts the ball 59 at one end and a shoulder 65 at the other end. The ball spring 63 tends to force the ball 59 against O-ring 58 and forms a sealed barrier between the primary chamber 7 and the apertures forward of the valve seat 51. A sliding cartridge 67 fits inside aperture 41. A cartridge tube 68 passes through the center of the cartridge 67 for its entire length. The rear end of the cartridge is a hollow shaft 69. The shaft 69 slides inside the valve seat 51 forming a seal with O-ring 55. A plurality of screws 71 pass through an equal number of counter bored holes 73 and are screwed into an equal number of holes 75 in the forward face of hollow body 1. The length of the screw 71 is sufficient to allow the sliding cartridge to move forward until surfaces 77 contact the heads of the screws 71. The rearward end of the hollow needle 3 is flanged at 79 and the flange screws into threads 81 on the inside of a cylindrical needle adapter 83. The needle adapter 83 is also threaded at its rearward end at 85 and is screwed into threads 87 on the inside of the sliding cartridge 67. The forward end of the needle 3 is cut at a slant to provide a sharp needle point 88

Continuing to refer to FIG. 3 a nose cone 89 of generally cylindrical shape fits over a neck 91 around the forwardmost end of the hollow body 1. A needle shaft 93 passes through an opening 95 in the center of the forwardmost surface of the nose cone 89. The nose cone, therefore, supports the needle and prevents bending or breaking. Threads 97 on the forward end of the sliding cartridge 67 engage with threads 99 on the inside of the nose cone 89. A plurality of swing arms 101 pivot on an equal number of pins 103 attached to the forward end of hollow body 1. An equal number of arm springs 105 also on the pins 103 engage surface 107 on hollow body 1 and surface 109 on the swing arms 101 and tend to force the rearward ends of the swing arms 101 outward and through slots 111 in the nose cone 89. Notches 113 engage surfaces 114 at the rear of slots 111 and prevent the nose cone 89 from moving forward.

Continuing to refer to FIG. 3 a tag 115 fits over the hollow needle 3. The tag is shaped to conform with the forward surface of the nose cone 89. The needle shaft 93 passes through a hole 117 in the center of the tag. The tag 115 is affixed to the forwardmost surface of the nose cone 89. In the preferred embodiment the tag is affixed to the nose cone with glue, but any fastening means including a hook-and-loop fastener may be used providing the bond between the tag and the nose cone may be broken without causing damage to either the nose cone or the tag. The forwardmost surface of the tag is coated with a strong adhesive. In the preferred embodiment tag glue, a glue widely used by ranchers and cowboys to affix various items to the hides of cattle, is used to coat the forwardmost face of the tag. The hollow needle 3, cartridge 67, nose cone 89, and tag 115 are connected and move forward and rearward as a unit. In a rearward position all of these elements are held in the rearward position by the swing arms 101 and their notches 113 contacting with surface 114 at the rearward end of nose cone slots 111.

In operation of the preferred embodiment the prongs 27 on the piston rod 29 are inserted through piston opening 33 into the piston core 38 in the piston 11 and piston rod 29 is rotated which causes the prongs 27 to contact the piston surface 37 and engages the piston rod 29 with the piston 11. The needle point 88 is inserted into the fluid to be injected and the piston rod 29 is pulled back which also pulls the piston 11 rearward and compresses piston spring 25. The fluid is drawn through the hollow needle 3, through cartridge tube 68, and into the primary chamber 7.

Referring again to FIG. 2 a plurality of marks 121 on piston rod 29 indicate the amount of fluid drawn into the primary chamber.

Referring again to FIG. 3 when the appropriate amount of fluid has been drawn into the primary chamber 7 and the piston rod 29 has been released spring 63 and the pressure of the fluid in primary chamber 7 press ball 59 against O-ring 58 which prevents fluid from flowing from the primary chamber. After the primary chamber is loaded, rotating the piston rod 29 in a reverse direction disengages the prongs 27 and allows the piston rod to be removed.

The loaded apparatus can be fired by a wide variety of guns, including compressed gas (e.g., $CO_2$) or air guns and chemical explosion guns. For example, a standard Palmer gun could be used. In addition, with relatively minor adaptation the device could be fired by a bow or cross-bow. The device may also be hand held and used for simple injection of preloaded fluids or operated on the end of a stick or rod.

Referring again to FIG. 3 upon impact with the target animal the hollow needle 3, the nose cone 89, the tag 115, and the sliding cartridge 67, are forced rearward. Surfaces 123 at the rearward end of nose cone 89 contact surfaces 125 on swing arms 101 which forces the rearward end of the swing arms toward the center of the hollow body 1 and compresses arm springs 105. Surfaces 109 move rearward passed notches 113 and the arm springs 105 force the swing arms 101 outward into slots 111 engaging notches 113 with surfaces 114 and holding the hollow needle 3, nose cone 89, and sliding cartridge 67 in a rearward position. O-ring 55 prevents fluid from leaking around the outside of the cartridge 67. The rearward end of cartridge tube 68 unseats ball 59 pushing it rearward from O-ring 58 and places primary chamber 7 in operational contact with hollow needle 3. Piston spring 25 and fluid pressure force piston 11 forward forcing the fluid in the primary chamber 7 through channels 127 in aperture 47 and slots 129 and through the cartridge tube 68 and the hollow needle 3 into the target animal. The adhesive on the forward face of the tag 115 holds the injection apparatus in place against the target animal during the time required for the injection to be completed.

Referring again to FIG. 2 a line 131 is attached at one end to a ring 132 on the tail cover 5. The line 131 may be used to retrieve the injection apparatus.

After the injection process is complete the injection apparatus is pulled from the target animal by reeling in the line or pulling the line by hand. The bond created by the adhesive between the tag 115 and the target animal is stronger than the bond between the tag and the nose cone 89. When the injection device is pulled from the animal, the tag breaks free of the injection apparatus and remains affixed to the target animal. In the preferred embodiment tags are provided in a plurality of colors and serve to mark the target animal for various purposes. For example, one color could be used to indicate one injection fluid and another color used to indicate a different injection fluid.

The injection apparatus is prepared for subsequent injections by manually depressing the swing arms 101, disengaging notches 113 and pulling the nose cone 89 forward. The distance between the heads of the screws 71 and the surfaces 77 on the sliding cartridge 67 is sufficient to allow the swing arms 101 and the nose cone 89 to be reset while preventing the nose cone 89 from being pulled completely away from the hollow body 1. A new tag 115 is affixed to the front of the nose cone. The piston rod 29 is reinserted into piston 11. A new dose of fluid is drawn into the primary chamber 7 by pulling back on the piston rod and the piston rod is removed.

In the preferred embodiment the hollow body 1 is injection molded plastic approximately five inches long and an inch and a quarter in diameter. The size of the hollow body is calculated to keep the injection apparatus as small and light as possible while maintaining a primary chamber 7 sufficiently large to accommodate relatively large doses necessary for medical treatment of large animals. The injection apparatus could be constructed in various sizes to accommodate either smaller or larger doses. While plastics such as cellulose-acetate-butyrate, polyester, polypropylene, and polyethylene could be used, the preferred material is polycarbonate. Other parts including the nose cone 89, cartridge 67, piston 11, valve seat 51, and tail cover 5, are also injection molded and of the same material as the hollow body. The needle 3 is preferably made from stainless steel. The tag 115 is preferably made of paper or other biodegradable material and shaped to conform with the front face of the nose cone 89, but could also be made of plastic or the like. The ball 59 is preferably made of a resilient material such as rubber or the like. The piston rod 29 is preferably made of steel or the like.

The shape of the nose cone 89 and the cushioning effected by its rearward movement upon impact act to prevent tissue and hide damage and trauma to the target animal.

The present invention is not limited to any particular components, materials, or configurations, and modifications of the invention will be apparent to those skilled in the art in light of the foregoing description. This description is intended to provide specific examples of individual embodiments which clearly disclose the present invention. Accordingly, the invention is not limited to these embodiments or to the use of elements having the specific configurations and shapes as presented herein. All alternative modifications and variations of the present invention which fall within the spirit and broad scope of the appended claims are included.

What is claimed is:

1. An apparatus for remotely injecting a fluid into an animal comprising:

a. a missile having a forward end and a rearward end;
   b. a fluid dispensing means at the forward end of the missile comprising:
      (1) a hollow body having a forward end and a rearward end;
      (2) a hollow needle extending through and fixed within the forward end of the hollow body;
      (3) a piston having front and rear faces slidably constrained within the hollow body, wherein a primary chamber suitable for containing a fluid is formed by the hollow body and the front face of the piston, wherein a secondary chamber is formed by the hollow body and the rear face of the piston;
      (4) a piston resilient means in operative contact with the piston for urging the piston toward the primary chamber;
      (5) an impact valve means in operational contact with the needle and with the primary chamber, wherein when the primary chamber is charged with a fluid and when the needle enters an animal the impact valve means opens and the resilient means causes the piston to force the fluid through the needle into the animal;
   c. a tag having front and rear faces fixed by the rear face to the forwardmost surface of the hollow body, wherein the front face of the tag is coated with adhesive means for attaching the missile to an animal; and
   d. means for remotely retrieving the apparatus.

2. The injection apparatus of claim 1, wherein the tag detaches from the hollow body when the missile is retrieved and remains attached to an animal.

3. The injection apparatus of claim 2, wherein the tag is colored.

4. An apparatus for remotely injecting a fluid into an animal comprising:

a. a missile having a forward end and a rearward end;

b. a fluid dispensing means at the forward end of the missile comprising:
   (1) a hollow body having a forward end and a rearward end, the rearward end of the hollow body being attached to the missile;
   (2) a piston having front and rear faces slidably constrained within the hollow body, wherein a primary chamber suitable for containing a fluid is formed by the hollow body and the front face of the piston, wherein a secondary chamber is formed by the hollow body and the rear face of the piston;
   (3) a piston resilient means in operative contact with the piston for urging the piston toward the primary chamber;
   (4) an impact valve assembly comprising:
      (a) a valve seat fixed within the forward section of the hollow body;
      (b) a hollow cartridge slideable within the forward section of the hollow body and within the valve seat and in operational contact with the primary chamber;
      (c) a hollow needle fixed to the forward edge of the cartridge and in operational contact with the cartridge and the primary chamber;
      (d) a ball within the forward section of the hollow body between the valve seat and the primary chamber;
      (e) a ball resilient means in operational contact with the ball for urging the ball forward against the valve seat;
      (f) a nose cone fixed to the forward end of the slideable cartridge wherein the outer rearward rim of the nose cone is slideable over the outer forward end of the hollow body, wherein the needle extends forward of the nose cone; and
      (g) a fastening means for holding the cartridge, needle, and nose cone in a rearward position;
   wherein when the primary chamber is charged with a fluid the ball resilient means forces the ball against the valve seat and prevents a fluid from leaving the primary chamber, wherein when the needle enters an animal the impact of the missile with an animal forces the nose cone, needle, cartridge, and ball rearward, wherein the nose cone, needle, cartridge, and ball are held in a rearward position by the fastening means, wherein the ball moves away from the valve seat allowing fluid to flow from the primary chamber, wherein the piston resilient means causes the piston to force fluid through the cartridge and the needle into an animal;

c. a piston rod insertable through the rearward end of the hollow body and the secondary chamber and engageable with the piston, wherein the piston rod can be pulled rearward manually causing the piston to move rearward and drawing fluid through the needle and cartridge into the primary chamber, and wherein the piston rod can be removed from the missile after the primary chamber is charged;

d. a tag having front and rear faces fixed by the rear face to the forwardmost surface of the nose cone, wherein the front face of the tag is coated with adhesive means for attaching the missile to an animal; and e. means for remotely retrieving the apparatus.

5. The injection apparatus of claim 4, wherein the tag detaches from the hollow body when the missile is retrieved and remains attached to an animal.

6. The injection apparatus of claim 5, wherein the tag is colored.

* * * * *